US011896343B2

United States Patent
Stratis et al.

(10) Patent No.: US 11,896,343 B2
(45) Date of Patent: *Feb. 13, 2024

(54) OPTICAL IMAGING DEVICE AND CAP

(71) Applicant: ARCHEOPTIX BIOMEDICAL INC., Kingston (CA)

(72) Inventors: Savvas Stratis, Kingston (CA); Jason David Richard Riley, Ottawa (CA)

(73) Assignee: ARCHEOPTIX BIOMEDICAL INC., Kingston (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,553

(22) Filed: Jul. 25, 2022

(65) Prior Publication Data

US 2023/0009107 A1   Jan. 12, 2023

Related U.S. Application Data

(63) Continuation of application No. 16/337,649, filed as application No. PCT/CA2016/051132 on Sep. 28, 2016, now Pat. No. 11,395,592.

(51) Int. Cl.
*A61B 5/00* (2006.01)
*A61B 5/02* (2006.01)

(52) U.S. Cl.
CPC ........ *A61B 5/0075* (2013.01); *A61B 5/02007* (2013.01); *A61B 5/6868* (2013.01); *A61B 2503/08* (2013.01); *A61B 2560/0406* (2013.01)

(58) Field of Classification Search
CPC .................................................. A61B 5/0075
See application file for complete search history.

(56) References Cited

U.S. PATENT DOCUMENTS

| 8,754,943 | B2 | 6/2014 | Klaerner et al. |
| 9,545,223 | B2 | 1/2017 | McFarlane et al. |
| 10,898,081 | B2 | 1/2021 | Stratis et al. |
| 2016/0296154 | A1 | 10/2016 | Riley et al. |

FOREIGN PATENT DOCUMENTS

| EP | 3064130 A1 | 9/2016 |
| WO | 2006/121833 A2 | 11/2006 |
| WO | 2011/084480 A1 | 7/2011 |

OTHER PUBLICATIONS

International Search Report and Written Opinion dated Jun. 27, 2017 issued in PCT/CA2016/051132.
Office Action dated Dec. 8, 2021 U.S. Appl. No. 16/337,649.
Notice of Allowance dated Mar. 16, 2022 received in U.S. Appl. No. 16/337,649.

*Primary Examiner* — Joseph M Santos Rodriguez
(74) *Attorney, Agent, or Firm* — Scully, Scott, Murphy & Presser, P.C.

(57) ABSTRACT

The present invention provides a removable optical imaging device cap for use with a near infrared (NIR) light optical imaging device for detecting intracranial hematoma.

16 Claims, 19 Drawing Sheets

SECTION A-A

OPTICAL IMAGING DEVICE AND CAP

CROSS-REFERENCE TO RELATED APPLICATION

This application is a continuation application of U.S. patent application Ser. No. 16/337,649 filed on Mar. 28, 2019, which claims the benefit of priority from International Application No. PCT/CA2016/051132 filed Sep. 28, 2016. The entire subject matter of the applications are incorporated herein by reference.

FIELD OF THE INVENTION

The present invention pertains to the field of optical imaging and in particular to devices for optical imaging to detect hematoma.

BACKGROUND

A hematoma is a localized collection of extravasated blood (e.g., blood from a ruptured blood vessel or the like), usually clotted, in an organ, space, or tissue; bruises and black eyes are familiar forms that are seldom serious. Hematomas can occur almost anywhere on the body including inside the skull, and are almost always present with a fracture; in minor injuries the blood is absorbed unless infection develops.

Hematomas inside the skull are particularly serious, because they can produce local pressure on the brain. The two most common kinds of these are epidural (outside the brain and its fibrous covering, the dura, but under the skull) and subdural (between the brain and its dura). Other types of hematomas occurring inside the skull include intracerebral (in the brain tissue) and subarachnoid (around the surfaces of the brain, between the dura and arachnoid membranes). Such hematomas can result from a number of causes such as head injury or head trauma as well as due to bleeding disorders or an aneurysm.

Subdural hematomas are usually the result of serious head injury. When a subdural hematoma occurs this way, it is typically called an acute subdural hematoma. Acute subdural hematomas are among the deadliest of head injuries as the bleeding fills the brain area very rapidly, thereby compressing brain tissue, which can lead to brain injury.

Subdural hematomas also can occur from a minor head injury, especially when the injured is elderly. Such hematomas can go unnoticed for a long period of time (e.g., many days to weeks) and are often called a chronic subdural hematoma. With any subdural hematoma, tiny veins between the surface of the brain and its dura stretch and tear, allowing blood to collect. In the elderly, such veins are often stretched because of brain atrophy or shrinkage and thus are more easily injured.

Because of the negative consequences associated with hematomas inside the head or skull, it is necessary to be able to identify and locate such hematomas inside the skull, such that appropriate medical and surgical procedures (e.g., evacuation of the hematoma) can be timely undertaken so as to reduce the chances for mortality and/or worsened outcome in survivors. Such timely undertakening is on the order of about 4 hours from occurrence of the injury and the evacuation of the hematoma.

The standard of care for detecting and imaging hematomas in traumatic head injury is either computed tomography (CT) scanning or magnetic resonance imaging (MRI). Acute hematomas represent the largest cause of death from head injury, with a mortality rate of 50-60%. Mortality rate can be lowered by diagnosis and treatment within the "golden hour" following traumatic head injury. However, CT and MRI are downstream technologies employed at large medical centers; accordingly, the time from injury to diagnosis is usually at least an hour, followed by subsequent treatment outside of the golden hour.

Chronic bleeds are often continuously monitored to check for evolution of the bleed. A secondary concern is the increasing belief that the number of CT scans in general needs to be reduced, particularly in pediatric populations, to reduce radiation exposure. Repeated CT is the method of choice to monitor chronic hematoma, which is a common form of Traumatic Brain Injury (TBI) in the pediatric population.

Although CT scanning and MRI are imaging techniques that can be used to identify and locate traumatic intracranial hematomas, all medical facilities (e.g., trauma centers) do not necessarily have immediate CT scanning and MRI capability on a 24/7 basis and thus it may not be possible in such cases for such scans to be performed so that an identified hematoma can be evacuated within the desired time frame. Also, timely identification of patients that require surgery for dealing with the hematoma can be more difficult in emergencies involving head trauma in underdeveloped areas of the world, or in areas which have limited access to trauma centers having 24/7 CT scanning or MRI capability or which have travel time issues from the site of the injury to the treatment facility, e.g., a rural area or a battlefield.

In such settings where a CT scan cannot be performed within the desired time frame, the primary method for identification of patients with hematomas is by means of a neurological exam. A neurological exam, however, is a poor substitute for a CT scan because no single physical sign can reliably indicate the presence of a hematoma. Focal neurological findings are found in only a fraction of patients with surgical hematomas. Coma has been reported to occur without the occurrence of a surgical hematoma in a large percentage of patients with severe head injury. Although patients with an intracranial hematoma will exhibit increased intracranial pressure (ICP), edema of the optic disk (papilledema), associated with ICP, is uncommon after head injury.

Even if the type of hematomas cannot be determined with certainty, the presence of any type of hematoma is the only information required in the field to triage a patient immediately to a hospital with neurosurgical diagnostic and operative capabilities.

It is therefore desirable to provide a device that would allow a clinician, medical personnel, emergency medical technician, field medic or the like to detect such a hematoma without requiring the use of imaging systems or techniques such as CT scan or MRI systems and in a wide range of settings including hospital ER settings and usage in the battlefield, rural areas or in less developed areas of the world.

There exist imaging technologies that utilize the Near Infra-Red (NIR) spectrum for detecting hematoma; examples are described in WO 2006/121833 and WO 2011/084480.

WO 2006/121833 discloses a system and method for determining a brain hematoma including a handheld device for emitting and detecting radiation with a removable light guide assembly. The method for determining a brain hematoma condition includes determining optical density of various regions of the brain using near infrared spectroscopy. In the above identified publication, the described device is positioned at a specific location of the head and data is acquired using the device. After acquiring data at this location, the device is re-located to another location of the head and another set of data is acquired at the new location. This relocation of the device and acquiring a set of data is repeated until the device has been placed at all possible or desired locations of the head.

WO 2011/084480 discloses methods, apparatus and devices for detecting a hematoma in tissue of a patient. In one aspect, such a method includes emitting near infrared light continuously into the tissue from a non-stationary near infrared light emitter and continuously monitoring the tissue using a non-stationary probe so as to continuously detect reflected light. The near infrared light is emitted at two distances from a brain of the patient, so the emitted light penetrates to two different depths. Such a method also includes applying a ratiometric analysis to the reflected light to distinguish a border between normal tissue and tissue exhibiting blood accumulation.

While these technologies allow for detection of hematoma using handheld devices, there remains a need for technologies that are suitable for use on uneven surfaces, while also effectively excluding ambient light infiltration, thereby resulting in an improved signal-to-noise ratio.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

An object of the present invention is to provide an optical imaging device and a removable cap for use with the imaging device. In accordance with an aspect of the present invention, there is provided an optical imaging device cap for use with a near infrared (NIR) light optical imaging device for imaging an object, wherein the imaging device comprises a body, at least three optical transceivers located within the body, and a mounting surface on which the device cap is mounted, the mounting surface having a generally planar mounting face and an outer wall extending from the periphery of the face, wherein the outer wall and the face define a mounting surface inner volume. The mounting face of the device comprises a plurality of openings arranged in a predetermined configuration and adapted to receive the at least three optical transceivers. The optical imaging device cap of the present invention comprises a bellow support plate and a deformable bellow sealingly engaged to the bellow support plate. The bellow support plate comprises a first support plate face shaped to engage the mounting face when the device cap is mounted within the mounting surface inner volume, a second support plate face configured to face a surface of the object to be imaged, and at least three deformable housings, each of the deformable housings being adapted to receive a light pipe and having a tip adapted to contact the surface of the object to be imaged, each of the light pipes corresponding to one of the at least three optical transceivers. The deformable bellow of the device cap has a generally C-shaped cross-sectional profile defining a first perimeter rim and a second perimeter rim, wherein the first perimeter rim sealingly engages the bellow support plate. In use, the second perimeter rim of the bellow contacts the surface of the object to be imaged and the bellow is deformed to allow the tips of the deformable housings to contact the surface of the object to be imaged.

In accordance with another aspect of the present invention, there is provided a near infrared (NIR) light optical imaging device for imaging an object, the imaging device comprising a body, at least three optical transceivers located within the body, a mounting surface located on the body, the mounting surface having a generally planar mounting face and an outer wall extending from the periphery of the face, wherein the outer wall and the face define a mounting surface inner volume, the mounting face comprising a plurality of openings arranged in a predetermined configuration and adapted to receive the at least three optical transceivers, and a device cap in accordance with the present invention mounted on the mounting surface.

DETAILED DESCRIPTION OF THE INVENTION

Definitions

Figure 1A:
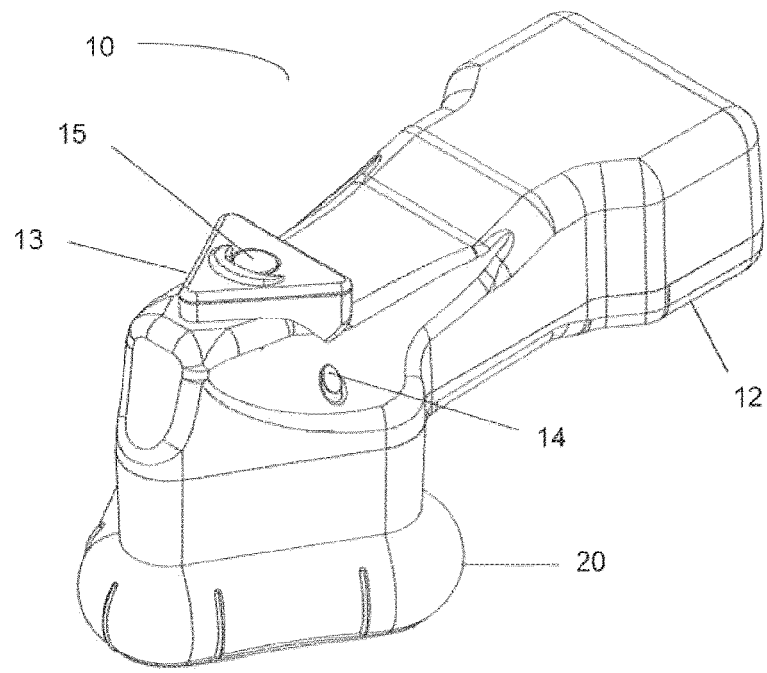
FIG. 1A is a perspective view of an optical imaging device in accordance with an embodiment of the present invention.
Figure 1B:
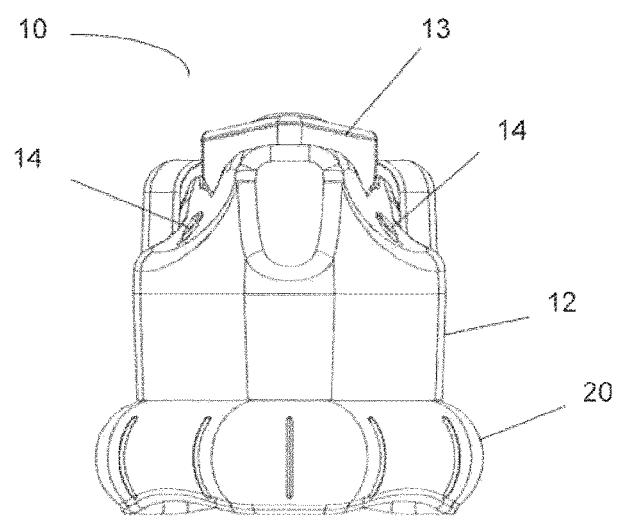
FIG. 1B is an end view of an optical imaging device in accordance with an embodiment of the present invention.

The terms "intracranial bleeding" and "intracranial hematoma" are intended to be used interchangeably, and encompass any accumulation of blood inside the skull of the patient, including the following: epidural hematoma, subdural hematoma, intracerebral hematoma, subarachnoid hematoma, and unilateral and bilateral hematoma.

An "epidural hematoma" shall be understood to mean a hematoma inside the head and where the blood collects or accumulates outside the brain and its fibrous covering, the dura, but under the skull.

A "subdural hematoma" shall be understood to mean a hematoma inside the head and where the blood collects or accumulates between the brain and its dura.

An "intracerebral hematoma" or "intracerebral hemorrhage" shall be understood to mean a hematoma inside the head and where the blood collects or accumulates in the brain tissue.

A "subarachnoid hematoma" or "subarachnoid hemorrhage" shall be understood to mean a hematoma inside the head and where the blood collects or accumulates around the surfaces of the brain, between the dura and arachnoid membranes.

An "extra cranial bleed" shall refer to any accumulation of blood outside the skull of the patient.

A "unilateral hematoma" shall be understood to mean a hematoma inside the head and in which blood collection or accumulation takes place on one side of the head.

A "bilateral hematoma" shall be understood to mean a hematoma inside the head and in which blood collection or accumulation takes place on both sides of the head.

The term "patient" and "subject" are used interchangeably, and shall be understood to include human beings, as well as other members of the animal kingdom.

The term "optical transceiver" is used to describe a fiber optic transmitter and receiver. It is also contemplated that, in the present disclosure, the term "optical transceiver" is also intended to refer to a device that acts solely as a light emitter (or light source) or a light detector.

Unless defined otherwise, all technical and scientific terms used herein have the same meaning as commonly understood by one of ordinary skill in the art to which this invention belongs.

As disclosed herein, there is provided a handheld optical imaging device for detection of intracranial hematoma, which employs near infrared (NIR) light detection. Identification of intracranial hematomas with NIR detection is made possible due to the fact that extravascular blood absorbs more NIR light than intravascular blood since there is a greater concentration of hemoglobin in the hematoma than in the brain tissue where blood is contained within vessels. Therefore, the absorbance of NIR light would be greater (and the reflected light less) in tissue containing a hematoma than in uninjured tissue.

The handheld optical imaging device therefore comprises a plurality of optical transceivers. In one embodiment, the plurality of optical transceivers comprises one or more NIR light sources and two or more MR light detectors.

In order to facilitate its use in the field, for example, in an ambulance, on the sidelines of a sporting event or on a military field of battle, the device has a body of a suitable size and shape for operation by hand and for convenient portability. Further the device must be robust in design so it is suitable for use in rugged or remote environments.

Furthermore, since the imaging device is typically used to image the head of a patient, the device should be presented for use in a clean state. Accordingly, the device is provided with a removable cap that encompasses all parts which may come into contact with the surface of the object being imaged in order to ensure cleanliness. The removable cap also must not compromise the light seal. It must be designed to be secure, while also being easily installed and removed.

Therefore, in accordance with the present invention, the handheld optical imaging device comprises a removable cap adapted for attachment to the body of the handheld device. The removable cap comprises a bellow support plate and a bellow mounted on the support plate. In one embodiment, the bellow support plate of the removable cap is mounted directly onto the body of the device on a suitably configured mounting surface. In one embodiment, the bellow support plate of the removable cap is attached to the body via a fixed base plate attached to the body of the device.

The device, in use, is passed over the surface of the object being imaged, e.g., a subject's skull, while the surface is irradiated with NIR. It is appreciated that a skull does not have a smooth surface, nor is a skull completely circular.

Accordingly, in accordance with the present invention, the removable cap must be suitable for use on an uneven surface, and should not cause undue discomfort to the subject undergoing irradiation.

The removable cap must be able to deliver the NIR light to and detect the NIR light from desired locations.

In one embodiment, the imaging device comprises at least three optical transceivers. In a preferred embodiment, the imaging device comprises three primary optical transceivers arranged in a triangular configuration. In a further preferred embodiment, the triangle is an equilateral triangle. In a further embodiment, the three primary optical transceivers comprise one NIR light source and two NIR light detectors. The equilateral triangular configuration ensures the adequate separation of the light detectors from the light source while maintaining the ability for all three housings to simultaneously contact a continuously varying $C^n$ (where n>0) surface. The equilateral triangle arrangement also provides a three point base when the device is placed on the object surface.

Each of the three primary optical transceivers in the triangular configuration is associated with a respective light pipe, and each light pipe is located in a respective primary deformable housing. Accordingly, in a preferred embodiment, the removable cap comprises a support plate provided with at least three primary deformable housings extending toward the surface being imaged.

It has been observed in end user experiments that, although the use of a removable cap having three non-deformable (fixed) housings can provide stability and control to some users, for others such a fixed configuration can result in difficulty in transitioning smoothly across a surface during the scanning process, and thus "over pressing", which may cause patient discomfort. These factors can lead to poor data acquisition due to the rough transitioning over the surface being imaged. It can also lead to patient movement, or "flinching" due to discomfort, which can result in scan interruption and thus poor data acquisition. Also, in the case of a head injury, such sudden head movements are unadvisable for the patient.

The present invention therefore provides a removable cap having deformable housings that do not cause undue discomfort to the subject undergoing the scanning process. Although such a configuration goes against pre-existing practices, data acquired using a device with deformable housings was gathered, and while the data was noisier than that acquired using a fixed housing configuration, the device in accordance with the present invention provided a correct measurement and is therefore suitable for the detection of intracranial hematoma. The configuration with deformable housings provides both ease of transit and prevents over pressure by users.

In a further preferred embodiment, the imaging device comprises two additional secondary optical transceivers located within the equilateral triangle formed by the primary optical transceivers. In this embodiment, these optical transceivers are NIR light detectors. Each of the secondary optical transceivers is associated with a respective light pipe, and each light pipe is located in a respective secondary deformable housing. Accordingly, two further points of contact with the surface of the object being imaged are provided by the additional secondary deformable housings. In a preferred embodiment, two secondary deformable housings are located at the edges of the triangle. This maintains the different detector separations in a linear arrangement, thereby allowing for improved optical sensitivity and accuracy of the device to detect inclusions.

Each of the primary and secondary deformable housings has a tip which will contact the surface of the object to be imaged during use.

In one embodiment, the light pipes are formed of an optically clear material. In one embodiment, the optically clear material is an optically clear acrylic. In one embodiment, the light pipes have matted interiors to ensure they do not cause internal light reflection. In a preferred embodiment, the light pipes are provided with rounded tips to ensure good contact with the surface of the object to be imaged, which is typically soft tissue.

In a further preferred embodiment, solid clear cores are employed to prevent capillary action bringing fluids or contaminants into the unit, thereby avoiding blockage of the pipes or damage to the sensors.

The removable cap must also be able to exclude external (ambient) light to ensure no tissue interactions with ambient light are measured alongside tissue interactions with intentionally delivered light, thereby improving the signal-to-noise ratio and reducing the incidence of false positive or negative readings. Accordingly, the removable cap is designed to prevent light leakage through sealing engagement between respective elements of the device, e.g., through fitting engagement between the removable cap and the mounting surface of the device, or where a base plate is employed, through fitting engagement between the fixed base plate and the removable cap. Fitting engagement between adjacent surfaces can be provided by the mating of raised profiles located around the circumference of an opening on one surface with corresponding recess on the adjacent surface. Light infiltration may also be prevented by the presence of an outer wall extending from the periphery of the mounting surface of the device to cover the interface between the mounting surface and the bellow support plate when the removable cap is installed.

Light leakage can also be minimized through the use of materials that do not internally reflect light, e.g., materials with a matte finish, or polymeric materials doped with NIR absorbants. In one embodiment, the support plate (and, when present, the base plate) is manufactured from a polymeric material. In a preferred embodiment, the polymeric material is ABS plastic. In one embodiment, the support plate and (if present) the base plate are each manufactured as a single piece.

The removable cap is also designed to prevent leakage between the cap and the surface of the object being imaged through the presence of a flexible bellow. The bellow provides an interface for the imaging device with the surface of the object to be imaged, which is typically the head of a patient. Accordingly, the bellow is preferably manufactured from a biocompatible material. In one embodiment, the bellow is manufactured from medical grade silicone. In one embodiment, the bellow is provided with a matte black finish.

Also, since the imaging device is used to image objects having an uneven surface (e.g., a skull), the bellow should be manufactured from a material having enough flexibility to conform to a continuously varying $C^n$ (where n>0) surface. Selection of a suitable durometer rating for the bellow ensures formation of a shielded environment. The bellow may be provided in any suitable shape as may be required for the application, including but not limited to circular or triangular. In one embodiment, the bellow has a triangular shape that reflects the shape of the active imaging area, in accordance with a preferred configuration, as will be discussed in more detail below. In this embodiment, the triangular profile of the bellow acts as a directional guide to the user to facilitate the imaging process. In a further embodiment, the bellow is provided with markings to provide additional information regarding the imaging elements, for example, by indicating the location of the outer periphery of the active area, or the location of one or more optical transceivers. These guide markings may be in the form of a raised rib, a groove, or a colored line or other marking located on the outer surface of the bellow.

In one embodiment, the bellow is attached to a bellow support plate, wherein the bellow support plate is configured to interface with the surface of the object to be imaged. In this regard, the support plate is configured to receive each of the plurality of light pipes, each of which corresponds to a respective optical transceiver located within the body of the imaging device.

The deformable housings are spring loaded and are designed to avoid any horizontal movement which might affect the data. The springs are hidden from the light path by the overlapping construction geometry to avoid light leakage. The springs are also situated between the detector and the light pipes to protect the detectors from any potential biological contamination (blood/hair). In one embodiment, the springs are held in place by a circular cap. In one embodiment, the springs are retained in place by spring plate. In one embodiment, the displacement of the light pipes within the housings is limited by stays.

The tips of the deformable housings of the bellow support plate sit above the lower perimeter rim of the bellow when not in use. It is therefore a requirement that the bellow be compressed to ensure the tips of the housings, and therefore the pipes housed therein, come into contact with the surface of the object to be imaged.

In addition, the removable cap should be designed to avoid formation of a "vacuum" seal, or suction effect, when in use, thereby ensuring that the device is able to move without hindrance across the surface to be imaged, while also avoiding light leakage. Accordingly, in one embodiment, the removable cap is provided with an air inflow system for allowing passage of air into the interior of the bellow when in use, without allowing infiltration of ambient light into the interior of the bellow.

In one embodiment of the air inflow system, the upper perimeter rim of the bellow is provided with grooves, or gaps, that allow air into the interior of the removable cap when installed on the body of the device while also preventing a direct line of sight between the exterior and interior. In one embodiment, air is allowed to pass through a small gap at the interface between the cap and body, without allowing light infiltration. In such an embodiment, one or more air holes are provided in the support plate to allow air into the interior of the bellow.

In one embodiment of the air inflow system, the lower perimeter rim of the bellow is provided with "S" shape grooves that ensure no direct line of sight between the exterior of the bellow and the interior. The gaps in the upper perimeter rim or the "S" shaped grooves the lower perimeter rim therefore act to trap the light while allowing an air passage to form, thereby preventing the flexible bellow from "sealing" to the surface of the object being imaged, allowing free travel of the device across the surface during use. The bellow material may also be provided with a matte finish to minimize light reflection.

The handheld optical imaging device comprises a body shaped and sized to fit within the hand of the user.

In accordance with the present invention, the presence or absence of hematoma or bleeding event is determined using the device by pressing the deformable bellow of the removable cap against the surface of the head of a patient to bring the tips of the deformable housings into contact with the surface of the head. While the tips are in contact with the surface of the head, the device is passed over the surface while irradiating the surface with NIR light. Presence or absence of a hematoma or bleeding event is signaled by illumination of a light located on the body of the device.

Accordingly, the optical imaging device also comprises a processor configured to process data collected by the NIR detectors, the processor having a display for indicating the presence of hematoma. The presence of the hematoma is based upon a measured characteristic of the infrared light passing through the tissue, for example, an optical density associated with a region of the brain. In one embodiment, the device comprises status indicator lights, which are provided to indicate the current status of the imaging process. For example, the status indicators may use different colours and/or blinking patterns to indicate, for example, that the device is in scanning mode, that an imaging error has occurred, or that a hematoma has been detected.

In one embodiment, the body is provided as a two-part housing, and contained within the body are the electronic components required for function. In one embodiment, the body is manufactured from a polymeric material. In one embodiment, the polymeric material is ABS plastic. In one embodiment, the polymeric material is flame retardant. The body may be may be manufactured using any suitable method known in the art, including, but not limited to, injection molding or extrusion processes or 3D printing processes.

The imaging process is activated using a power switch located on the body of the device. In one embodiment, the power switch is provided as a "deadman's switch", where the imaging process is activated only when the button is depressed. In one embodiment, the device is provided with two switches, one on each side of the body to allow use by both left handed and right handed users. In a preferred embodiment, the device is powered by a battery for ease of portability and use in remote areas where access to a power supply may not readily be available.

In accordance with one embodiment of the present invention, as depicted in FIGS. 1-6, the device comprises a removable cap 20 attached directly to body 12 of device 10 via mounting surface 22 of the body. In this embodiment, mounting surface 22 has a generally planar mounting face 23 and outer wall 25 extending from the periphery of the face 23 which together define mounting surface inner volume 24 in which removable cap 20 is mounted.

The mounting face comprises a plurality of openings adapted to receive optical transceivers located within the body of device 10. Removable cap 20 comprising bellow support plate 40 and deformable bellow 60 sealingly engaged to the support plate. Bellow support plate 40 comprises first support plate face 5 shaped to engage the mounting face 23 when removable cap 20 is mounted within the mounting surface inner volume 24, and second support plate face 6 configured to face a surface of the object to be imaged.

Details of the removable cap in accordance with this embodiment are depicted in FIGS. 3 to 6.

In this embodiment, bellow support plate 40 further comprises two deformable housings 43B and one deformable housing 43A, each of the housings 43A and 43B being adapted to receive a respective light pipe 35A or 35B. The three housings 43A and 43B are arranged in an equilateral triangular configuration.

In this embodiment, further points of contact are provided by two additional deformable housings 43C, each of which are adapted to receive a light pipe 35C. In this embodiment, two deformable housings 43C are located at edges of the triangle, thereby maintaining the different detector separations in a linear arrangement, thereby allowing for improved optical sensitivity and accuracy of the device to detect inclusions.

In this embodiment, each of the light pipes corresponds to a respective optical transceiver located in the body of the device. In this embodiment, the optical transceiver corresponding to light pipe 35A is a NIR light source, and the optical transceivers corresponding to light pipes 35B and 35C are NIR light detectors.

In this embodiment, each of the deformable housings 43A-C extends from second support plate face 6 towards the surface of the object being imaged. The tips of each of the deformable housings are adapted to contact the surface of the object to be imaged.

Figure 5:
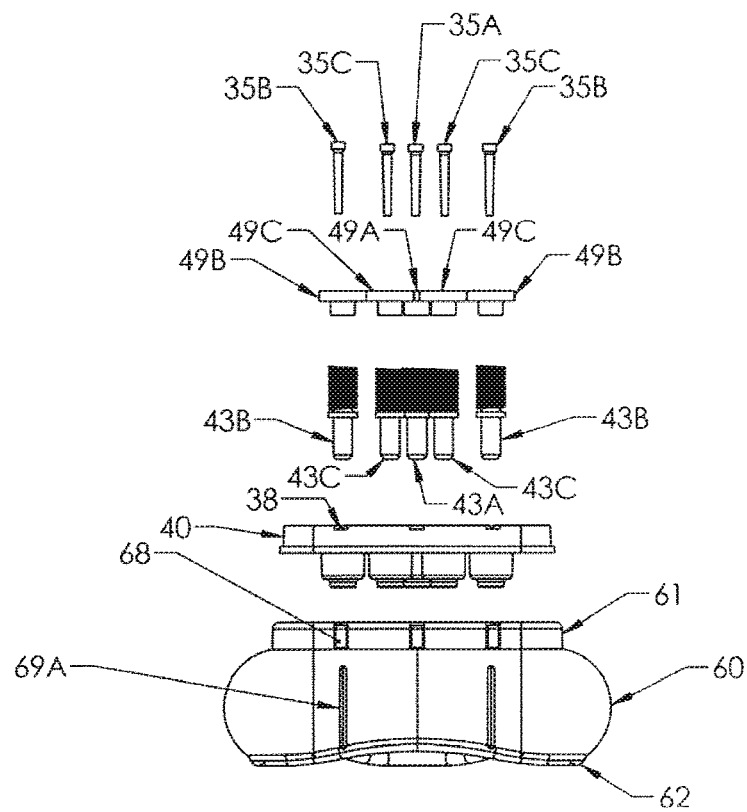
FIG. 5 is an exploded view of a removable cap in accordance with one embodiment of the present invention.
Figure 6:
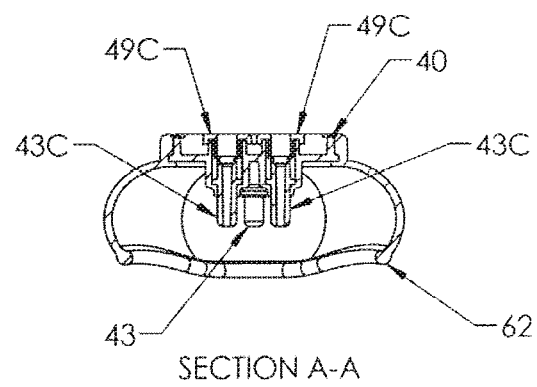
FIG. 6 is a cross sectional view of a removable cap in accordance with one embodiment of the present invention.
Figure 7A:
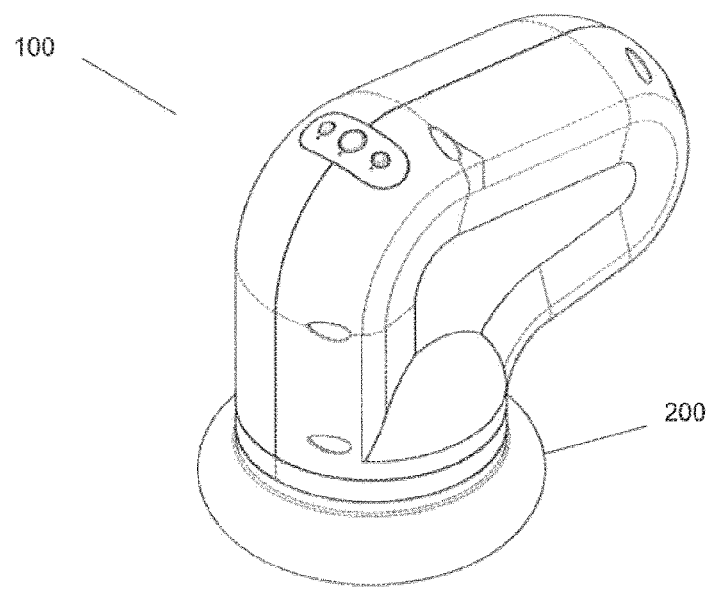
FIGS. 7A-C illustrate perspective, front and back views of an optical imaging device in accordance with an embodiment of the present invention.
Figure 7B:
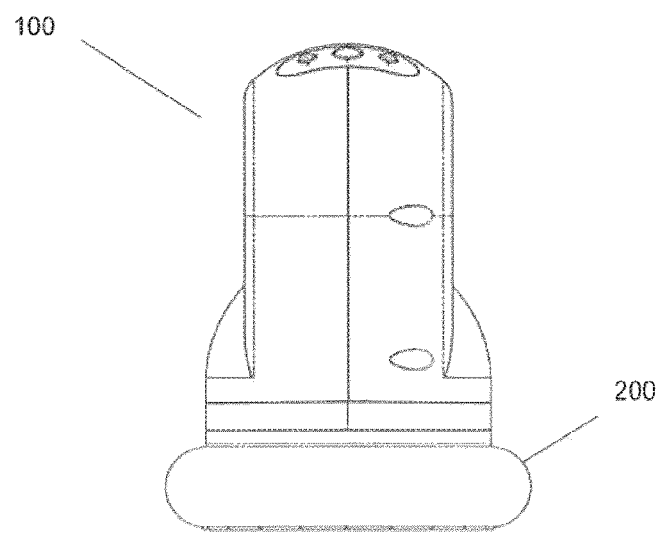
Figure 7C:
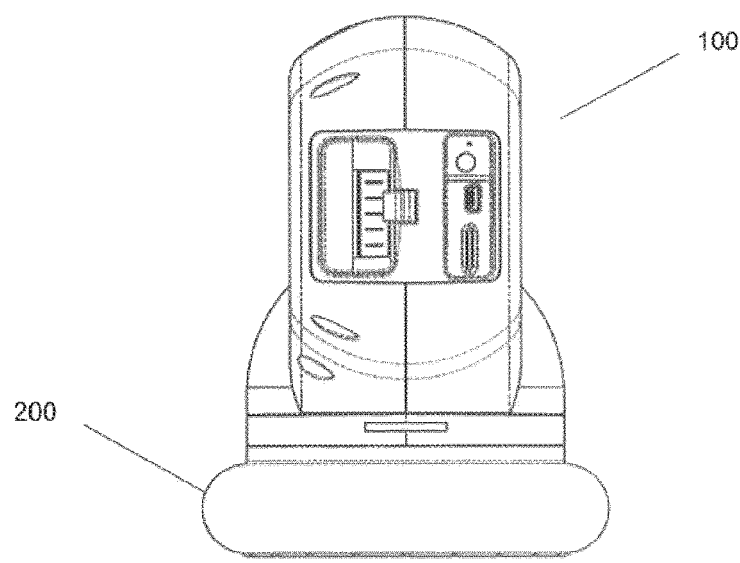

In this embodiment, and as shown in FIGS. 5 and 6, deformable housings 43A-C are spring loaded and are designed to avoid any horizontal movement which might affect the data. Springs 47 are hidden from the light path by the overlapping construction geometry to avoid light leakage. The springs are also situated between the detector and the light pipes to protect the detectors from any potential biological contamination (blood/hair). Springs 47 are retained in place by a respective cap 49A-C, and the displacement of each of the light pipes 35A-C within the housings is limited by a respective stay 48. Each of caps 49A-C is adapted to engage a respective optical transceiver.

In this embodiment, light infiltration is prevented by fitting engagement between the bellow support plate 40 and outer wall 25 extending from the periphery of the mounting surface 22. The outer wall 25 is provided to cover the interface between the bellow support plate 40 and mounting face 23 when removable cap 20 is installed.

In this embodiment, deformable bellow 60 has a generally C-shaped cross-sectional profile defining first, upper perimeter rim 61 and second, lower perimeter rim 62. In this embodiment, first perimeter rim 61 sealingly engages bellow support plate 40, and fits within outer wall 25 of mounting surface 22 when cap 20 is mounted within the mounting surface inner volume 24. In this embodiment, cap 20 is held secure to the mounting surface by resilient and frictional fit of upper perimeter rim 61 within outer walls 25, without necessitating the use of additional attachment means.

The tips of the deformable housings 43A-C of bellow support plate 40 sit above second perimeter rim 62 of bellow 60 when not in use. It is therefore a requirement that bellow 60 be compressed to ensure the tips of the housings, and therefore the fibers housed therein, come into contact with the surface of the object to be imaged. Accordingly, in use, the lower perimeter rim 62 of bellow 60 contacts the surface of the object to be imaged and the bellow is deformed to allow the tips of the deformable housings to contact the surface of the object to be imaged.

Figure 3:
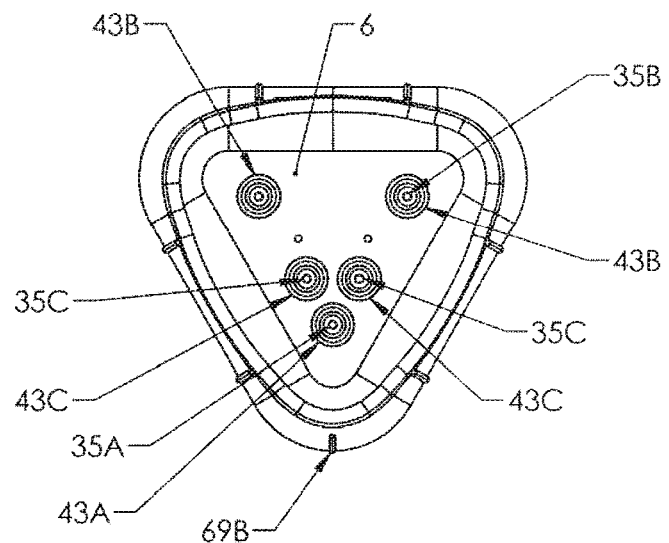
FIG. 3 is a bottom view of a removable cap in accordance with one embodiment of the present invention.
Figure 4:
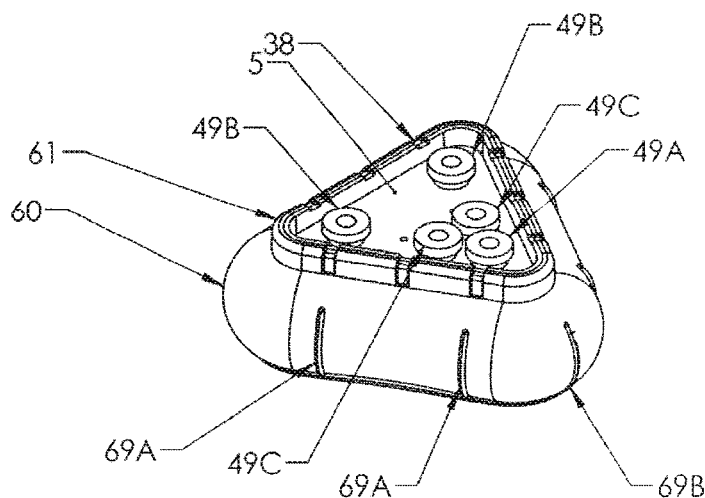
FIG. 4 is a perspective view of a removable cap in accordance with one embodiment of the present invention.

As shown in FIGS. 3 and 4, bellow 60 is provided with markers 69A located to indicate the outer limits of the active imaging area within the bellow, and marker 69B located to indicate the location of the irradiating optical transceiver, all of which provide guidance to the user to ensure complete coverage of the surface being imaged, thereby facilitating the imaging process.

In this embodiment, the removable cap and bellow are provided in a triangular shape to correspond to the triangular configuration of the optical transceivers.

In this embodiment, upper perimeter rim 61 of bellow 60 is provided with a series of grooves 38 that allow air into the interior of the removable cap when installed on the body of the device through gap 18 at the interface between cap 20 and body 12, without allowing light infiltration. In this embodiment, the air inflow system further comprises openings 68 on the bellow support plate corresponding to the grooves in the first perimeter rim of the bellow. In this embodiment, air holes 46 are also provided in support plate 40 to allow air into the interior of the bellow, thereby preventing suction events when bellow 60 is pressed to the surface of the object being imaged.

In this embodiment, device 10 includes status indicator light 13, which are provided to indicate the current status of the imaging process. For example, status indicator light 13 uses a different colour to indicate that the device is in scanning mode (e.g., green), that an imaging error has occurred (e.g., orange), or that a hematoma has been detected (e.g., red).

In this embodiment, device 10 includes two power buttons 14, one on each side of the body to allow use by both left handed and right handed users, each button provided as a "deadman's switch", where the imaging process is activated only when the button is depressed.

Figure 8:
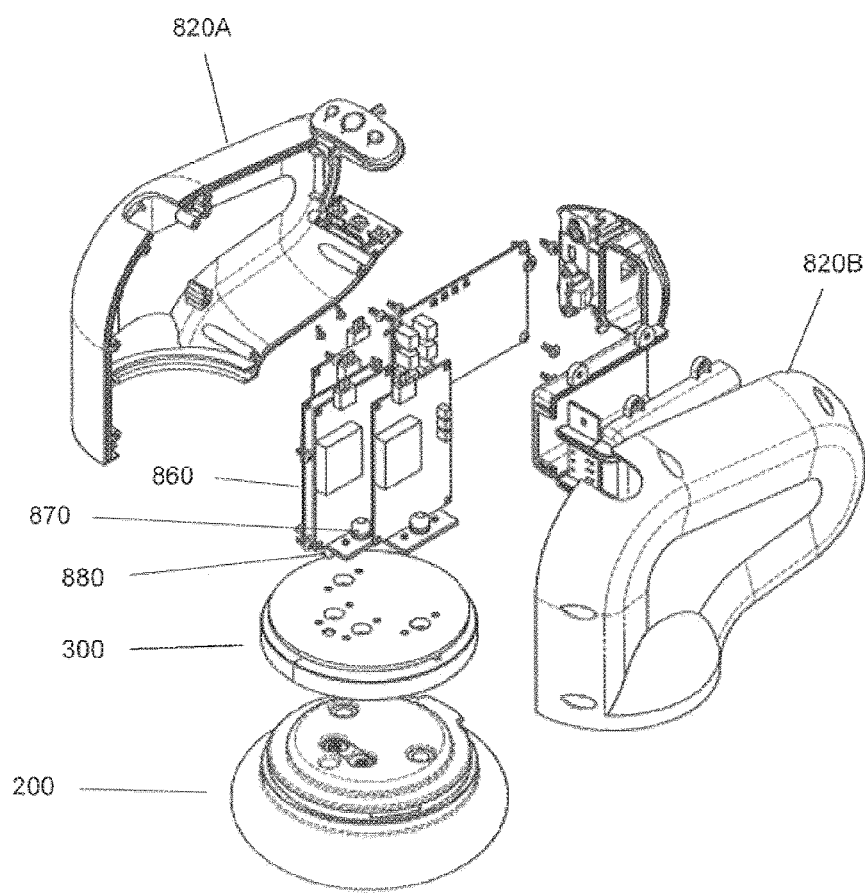
FIG. 8 is an exploded view of an optical imaging device in accordance with an embodiment of the present invention.
Figure 9:
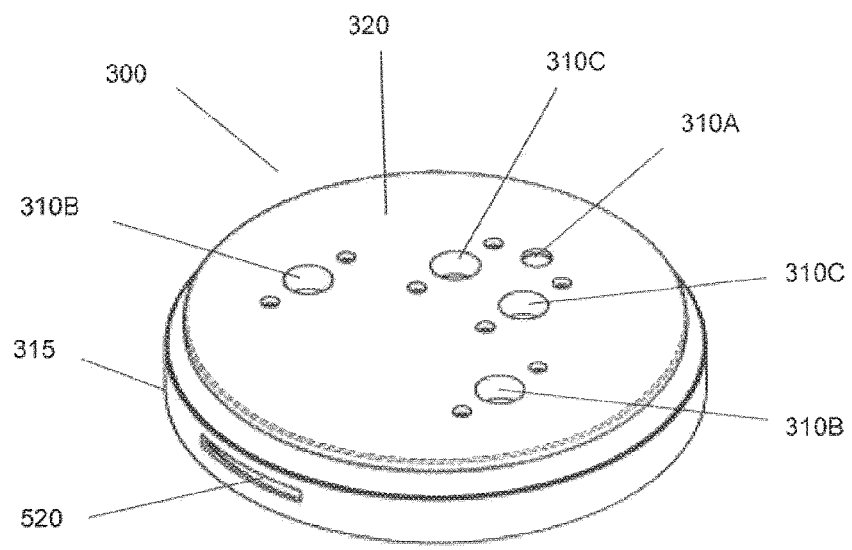
FIG. 9 is a top perspective view of a base plate in accordance with one embodiment of the present invention.
Figure 10:
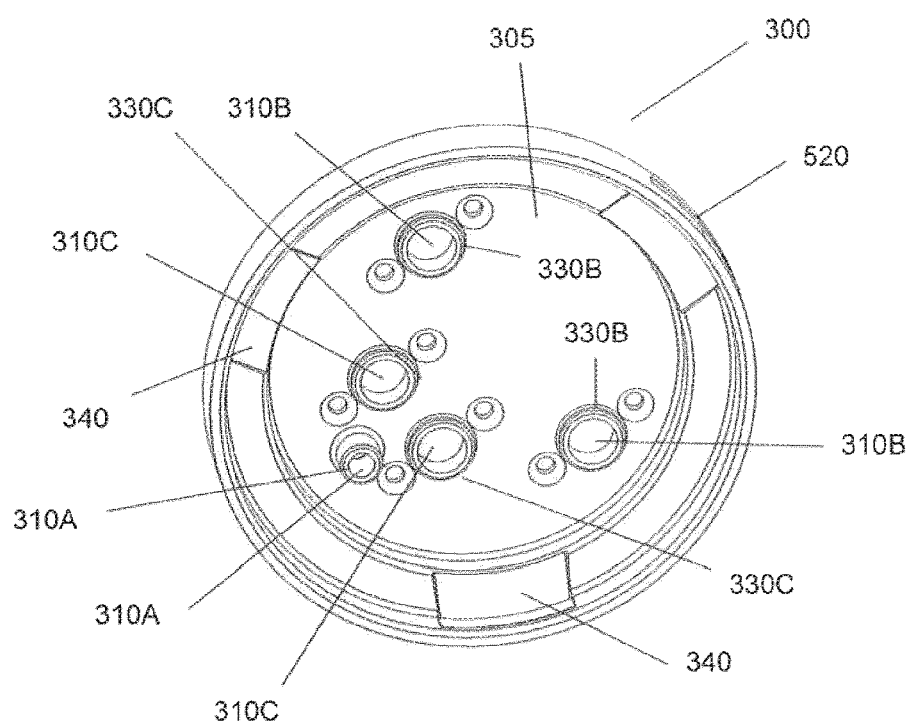
FIG. 10 is a bottom perspective view of the base plate of FIG. 9.

In accordance with a further embodiment of the present invention, as depicted in FIGS. 7 to 15, the device comprises a fixed base plate 300 configured to receive the removable cap 200. As depicted in FIGS. 9 and 10, the fixed base plate 300 has a generally planar body 320 comprising a base plate face 305 and a plurality of base plate openings 310A-C in the planar body arranged in a predetermined configuration. The base plate openings 310A-C are adapted to receive respective optical transceivers. The fixed base plate 300 also comprises an outer wall 315 extending from the periphery of the base plate face 305. The outer wall 315 and the base plate face 305 together define a base plate inner volume.

In this embodiment, light infiltration is prevented by fitting engagement between the fixed base plate 300 and the bellow support plate 400 provided by the mating of raised profiles 330A-C located around the circumference of each the openings 310A-C for the optical transceivers on the fixed base plate 300 with corresponding recesses 415A-C on the bellow support plate 400, which is described in further detail below.

In this embodiment, light infiltration is also prevented by the presence of the outer wall 315 extending from the periphery of the fixed base plate 300. The outer wall 315 is provided to cover the interface between the fixed base plate 300 and the bellow support plate 400 when the removable cap is installed.

Figure 12A:
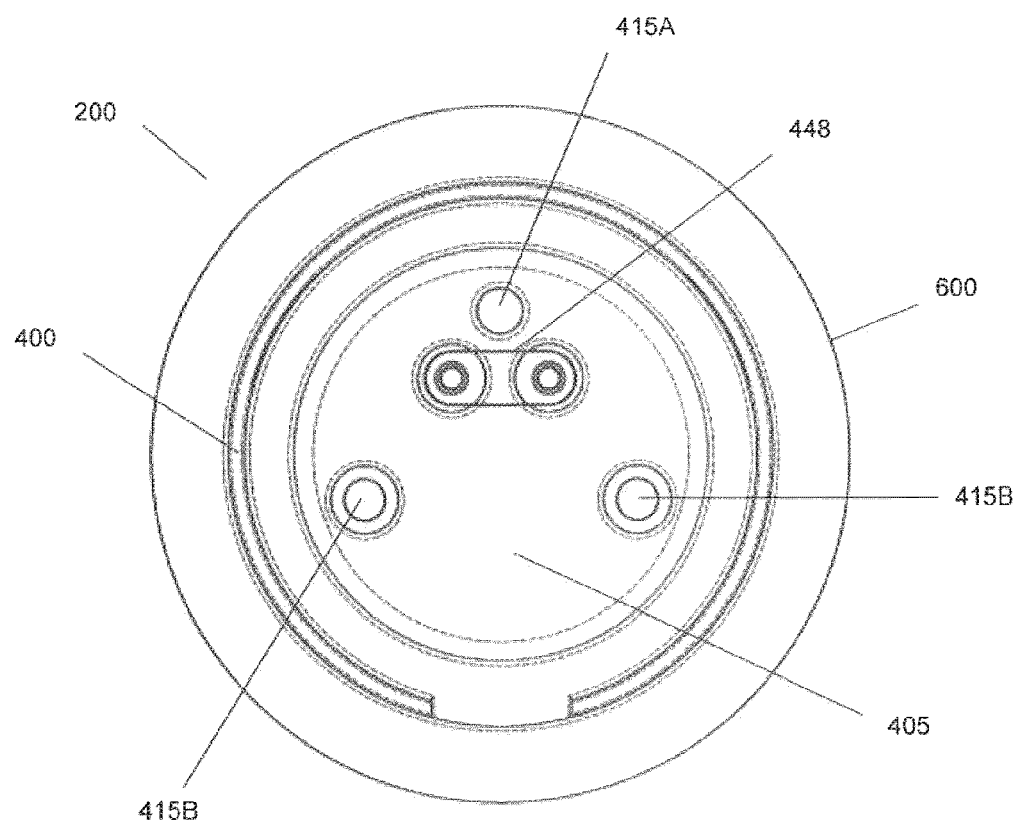
FIG. 12A is top a top view of the bellow support plate of FIG. 11.
Figure 12B:
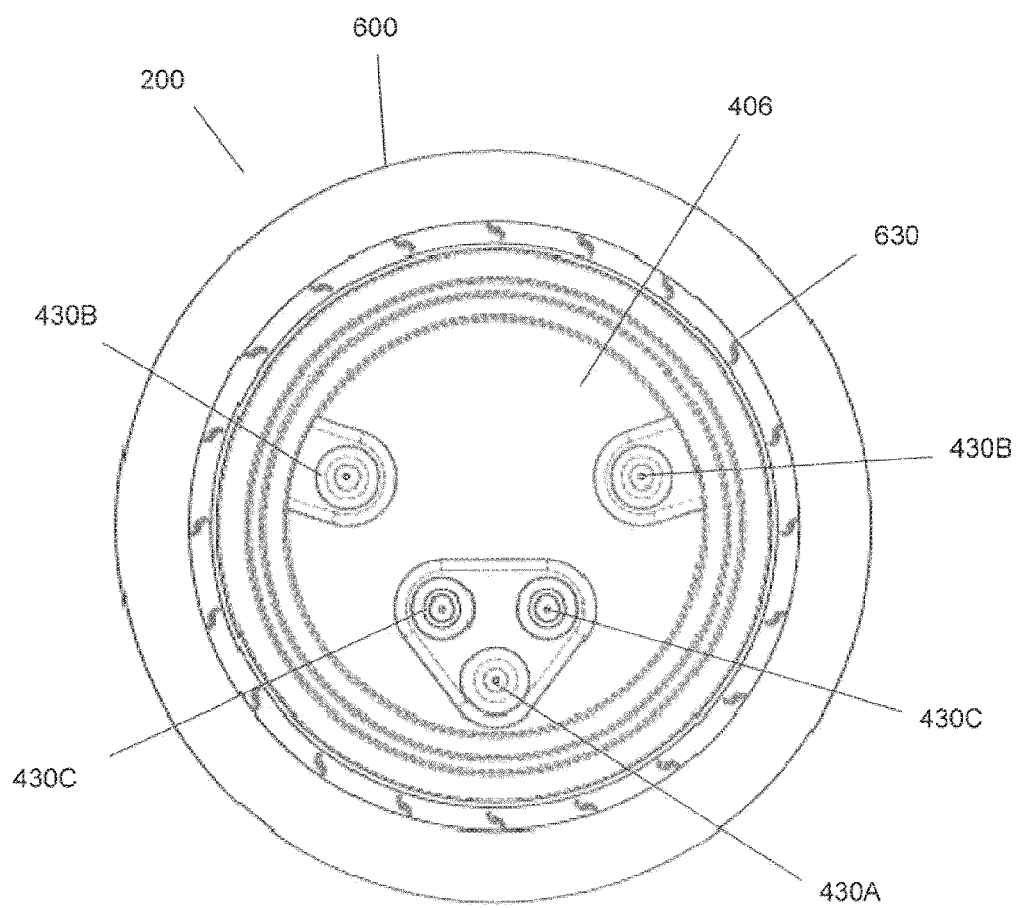
FIG. 12B is a bottom view of the bellow support plate of FIG. 11.
Figure 13:
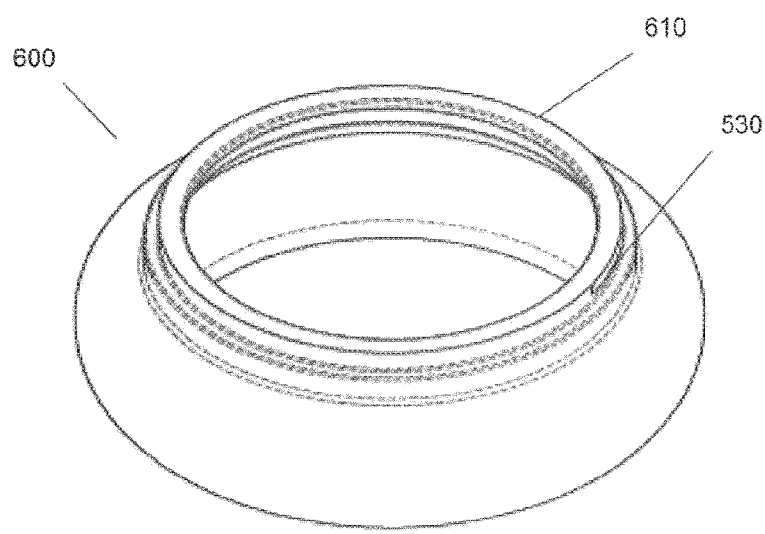
FIG. 13 is a perspective view of a bellow in accordance with one embodiment of the present invention.
Figure 14:
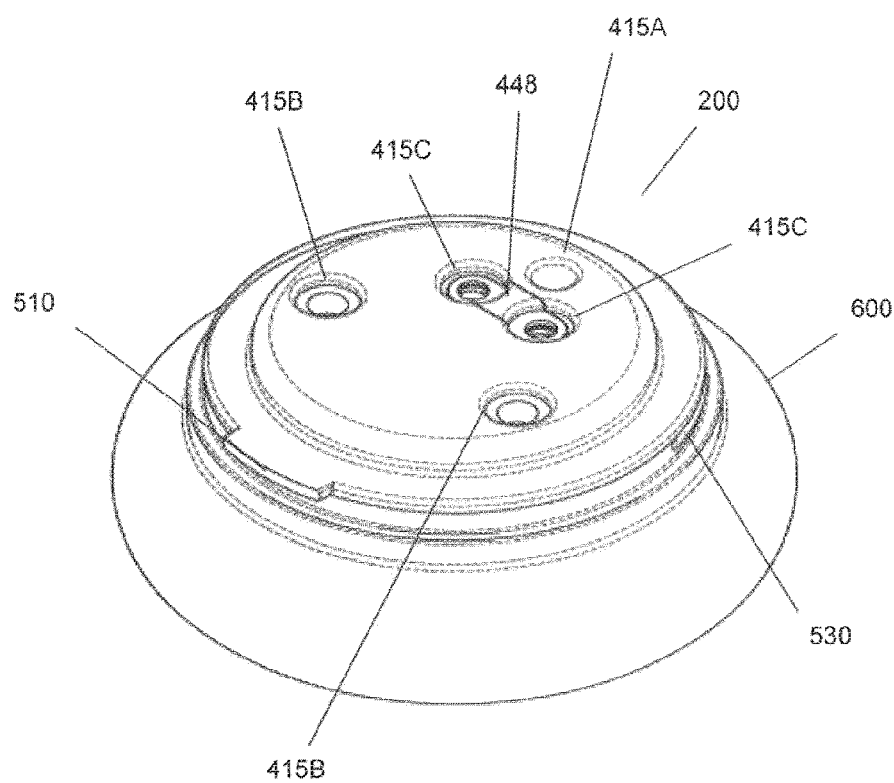
FIG. 14 is a perspective view of a removable cap in accordance with one embodiment of the present invention.
Figure 15:
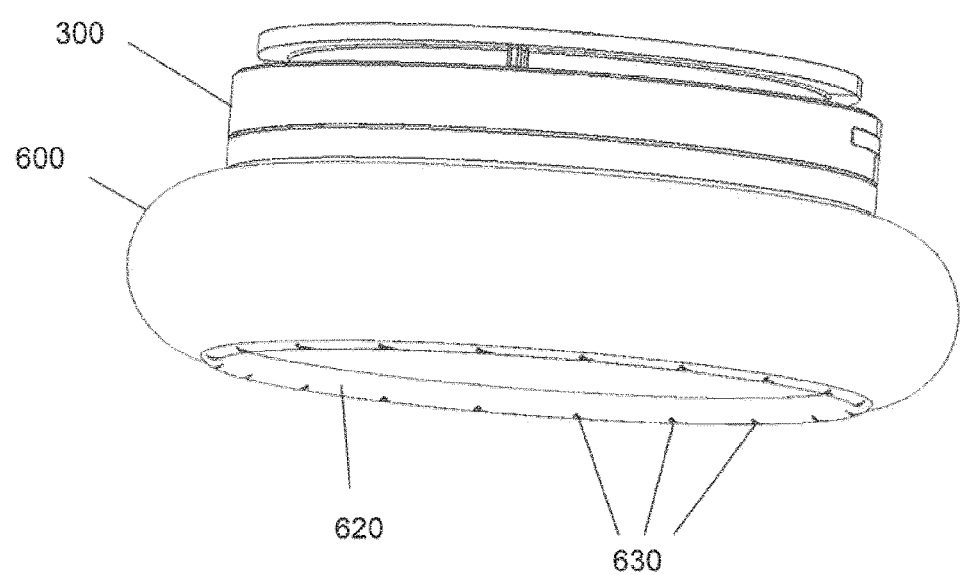
FIG. 15 is a perspective view of a removable cap assembled with a base plate in accordance with one embodiment of the present invention.

In the embodiment depicted in FIGS. 12A and 12B, the removable optical imaging device cap 200 comprises bellow support plate 400 and deformable bellow 600.

In this embodiment, bellow support plate 400 comprises first portion 410 and second portion 420. The first portion 410 of bellow support plate 400 is shaped to fit within the base plate inner volume, such that first support plate face 405 fittingly engages fixed base plate face 305 when the first portion 410 is located within the base plate inner volume. The bellow support plate 400 also has a second support plate face 406 configured to face a surface of the body to be imaged, and three primary deformable housings 430AB arranged in an equilateral triangle configuration and two secondary deformable housings 430C located along the edge of the triangle, all of which extend from the second support plate face 406 toward the surface being imaged. Each of deformable housings 430A-C is adapted to receive therein a light pipe (not shown), each of which corresponds to a respective optical transceivers in the body of the device. In addition, each of the deformable housings have a tip (not shown) adapted to contact the surface of the object to be imaged.

The second portion of bellow support plate 400 is adapted to sealingly engage deformable bellow 600 to eliminate infiltration of ambient light to the detectors.

Figure 11:
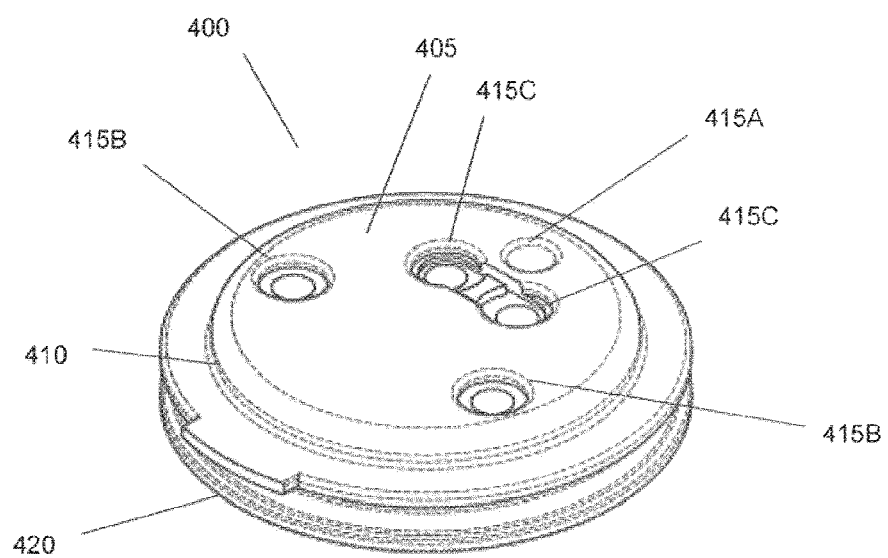
FIG. 11 is a perspective view of a bellow support plate in accordance with one embodiment of the present invention.

As discussed above, bellow support plate 400 comprises recesses/dimples 415A-C suitably sized and located to receive raised profiles 330A-C surrounding openings 310A-C for the optical transceivers on fixed base plate 300. FIG. 11 illustrates one embodiment of recessed openings 415A-C on bellow support plate 400. The mating of recessed openings 415A-C with respective raised profiles 330A-C is designed to prevent light leakage between light source and detectors at the connection plane for removable cap 200.

Accordingly, each of the deformable housings 430A-C on bellow support plate 400 is provided to correspond to a respective optical transceivers. Each housing 430A-C contains a light pipe (not shown) formed of an optically clear material.

The deformable housings are spring loaded and are designed to avoid any horizontal movement which might affect the data. The springs are hidden from the light path by the overlapping construction geometry to avoid light leakage, and are situated between the detector and the light pipes to protect the detectors from any potential biological contamination (blood/hair). A spring plate 448 may be employed to retain springs in place.

As depicted in FIG. 12B, bellow 600 is provided with "S" shaped grooves along the rim to ensure a light seal while preventing a suction effect when the rim of the bellow is in contact with the surface being imaged. In this embodiment, the "S" shaped grooves and the matte finish combine to trap the light while allowing an air passage to form, thereby preventing the molded silicone bellow from "sealing" to the surface of the object being imaged, allowing free travel of the device across the surface during use.

In accordance with the embodiment depicted in FIGS. 10 and 11, there is provided an attachment means for reversibly attaching bellow support plate 400 to fixed base plate 300.

In this embodiment, the attachment means is provided by a tab and slot mechanism, wherein tab 510 is located on bellow support plate 400 and slot 520 is located on outer wall 315 of base plate 300. To form a seal, tab 510 is inserted into slot 520, and fixed base plate 300 then "hinges" into place and a seal is formed between fixed base plate 300 and bellow support plate 400. In this embodiment, the attachment means further comprises one or more "soft buttons" 530 located on the outer edge of the bellow that are positioned to "click" into recesses 340 located on the inner surface of outer wall 315.

The attachment means is configured such that when tab 510 is engaged in slot 520, recesses 415A-C and respective raised profiles 330A-C are aligned. This configuration also provides an optimum fit of the transceivers into to the recesses/dimples on bellow support plate 400.

In one embodiment, the attachment means is provided by a bayonet style fitting, although any means that provides an easy "in/out" connection is suitable and considered to be within the scope of the present invention.

The invention will now be described with reference to specific examples. It will be understood that the following examples are intended to describe embodiments of the invention and are not intended to limit the invention in any way.

EXAMPLES

Example 1: Handheld Optical Imaging Device

FIGS. 1A and B and 2A and B depict one embodiment of a handheld optical imaging device 10 in accordance with the present invention. The optical imaging device 10 comprises a removable cap 20 attached to body 12 suitably sized and shaped to easily fit within the hand of a user.

In the embodiment depicted in FIGS. 1A and B and 2A and B the device comprises one NIR light source 180, and four NIR light detectors 170.

Figure 2A:
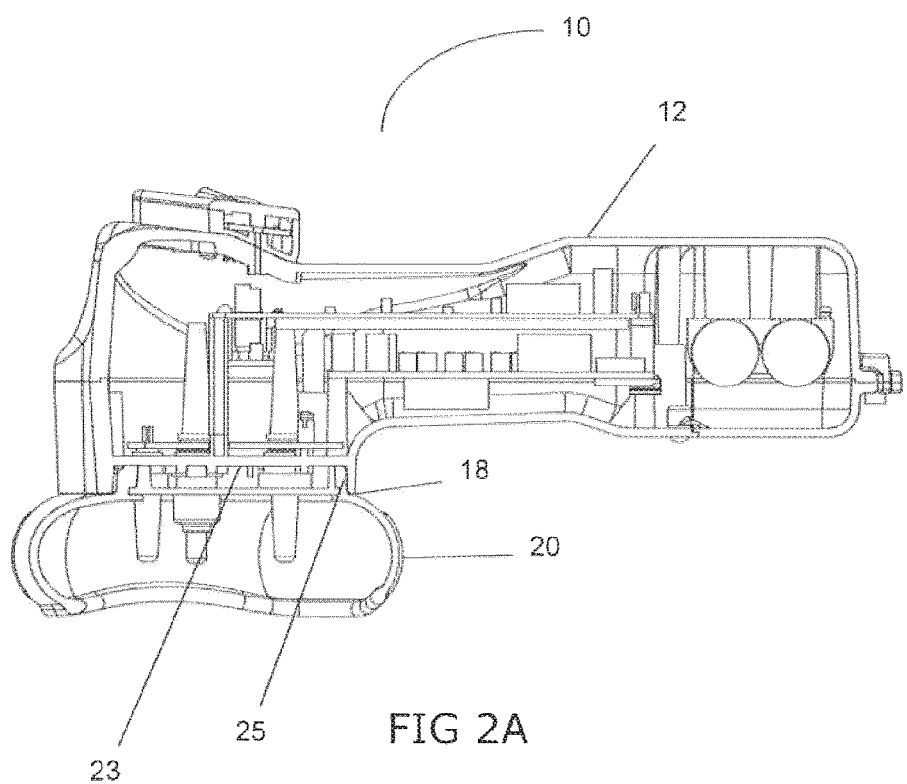
FIG. 2A is a cross sectional side view of an optical imaging device in accordance with an embodiment of the present invention.
Figure 2B:
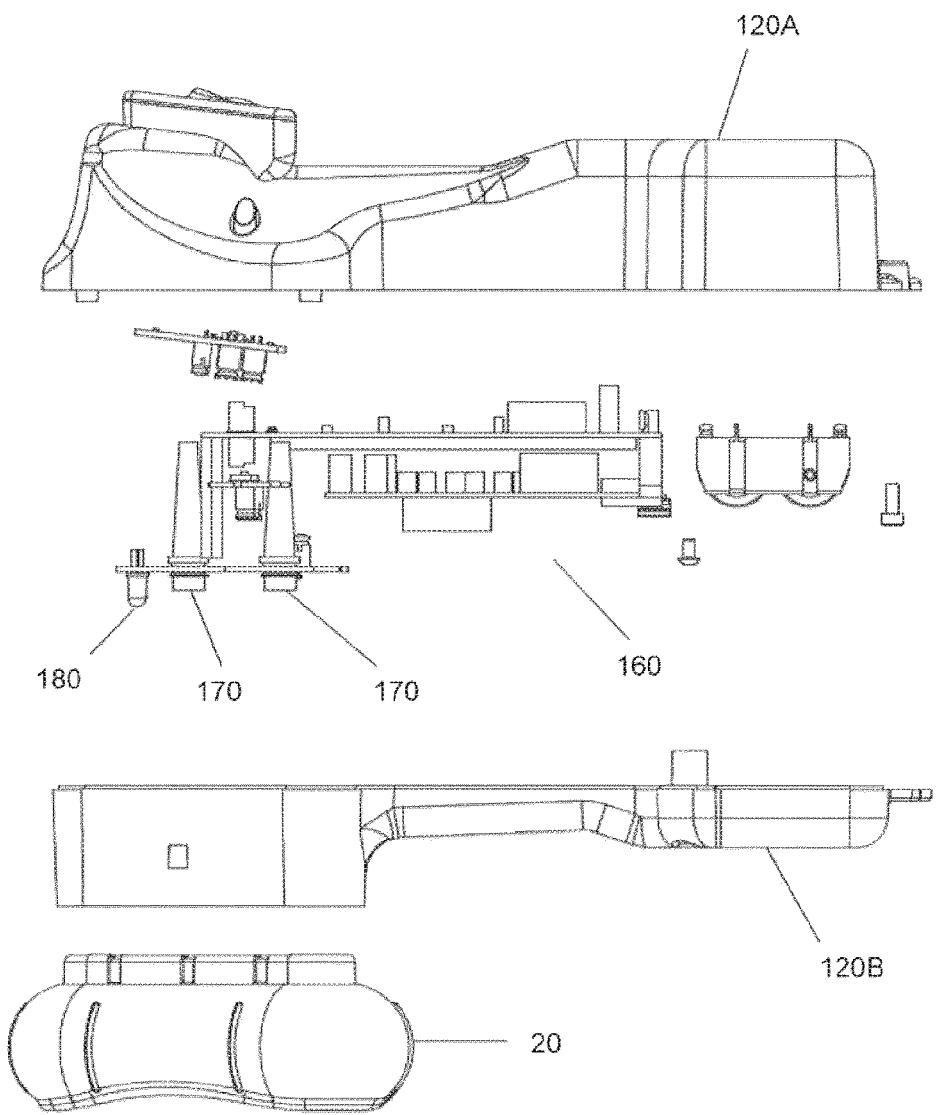
FIG. 2B is an exploded side view of an optical imaging device in accordance with an embodiment of the present invention

An exploded view of this embodiment of the optical imaging device is provided in FIG. 2B. FIG. 2B depicts two part housing 120A,B that forms the body. Housing 120A,B is designed to contain within it the electronics 160 required for function, as well as the processor required to analyze the data obtained during the imaging process.

Example 2: Handheld Optical Imaging Device

FIGS. 7A-C and 8 depict another embodiment of a handheld optical imaging device 100 in accordance with the present invention. The optical imaging device 100 comprises a removable cap 200 attached to a body suitably sized and shaped to easily fit within the hand of a user.

In the embodiment depicted in FIGS. 7A-C and 8, the device comprises one NIR light source 880, and four NIR light detectors 870.

An exploded view of this embodiment of the optical imaging device is provided in FIG. 8. FIG. 8 depicts two part housing 820A,B that forms the body. Housing 820A,B is designed to contain within it the electronics 860 required for function, as well as the processor required to analyze the data obtained during the imaging process.

Prior to use, removable cap 200 is installed via attachment to fixed base plate 300. The device is powered by a battery (not shown).

Example 3: Hybrid Military Flashlight/Optical Imaging Device

Figure 16:
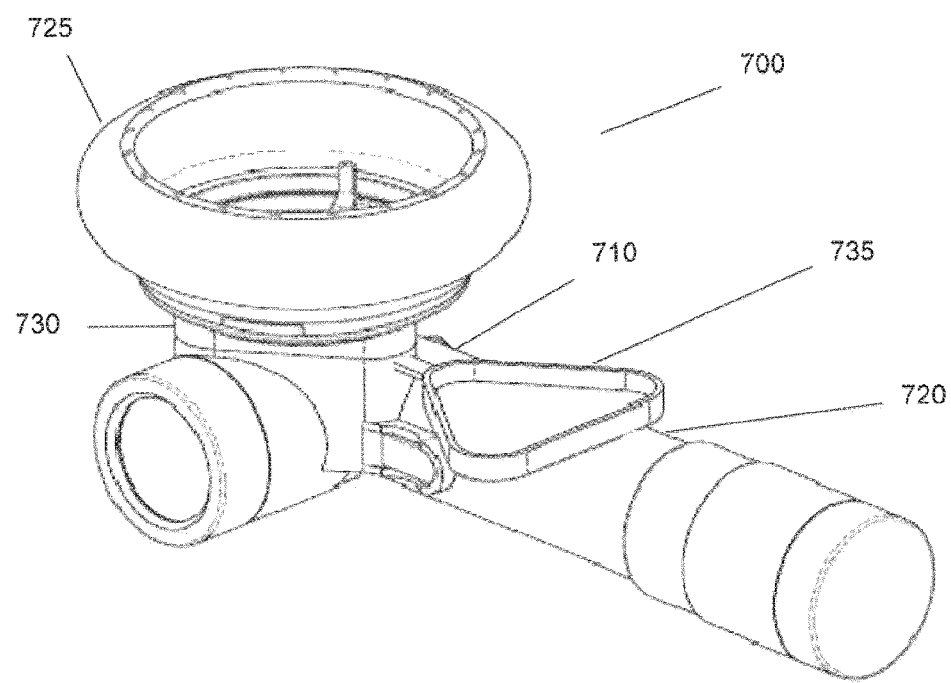
FIG. 16 is a perspective view of an optical imaging device in accordance with an embodiment of the present invention, with the removable cap attached.
Figure 17:
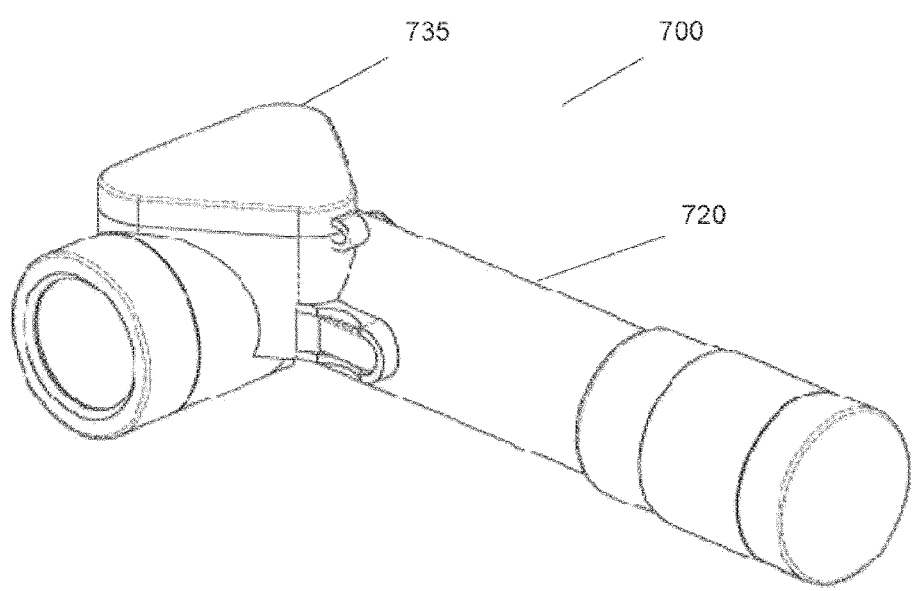
FIG. 17 is a perspective view of an optical imaging device in accordance with an embodiment of the present invention, with the removable cap removed.
Figure 18:
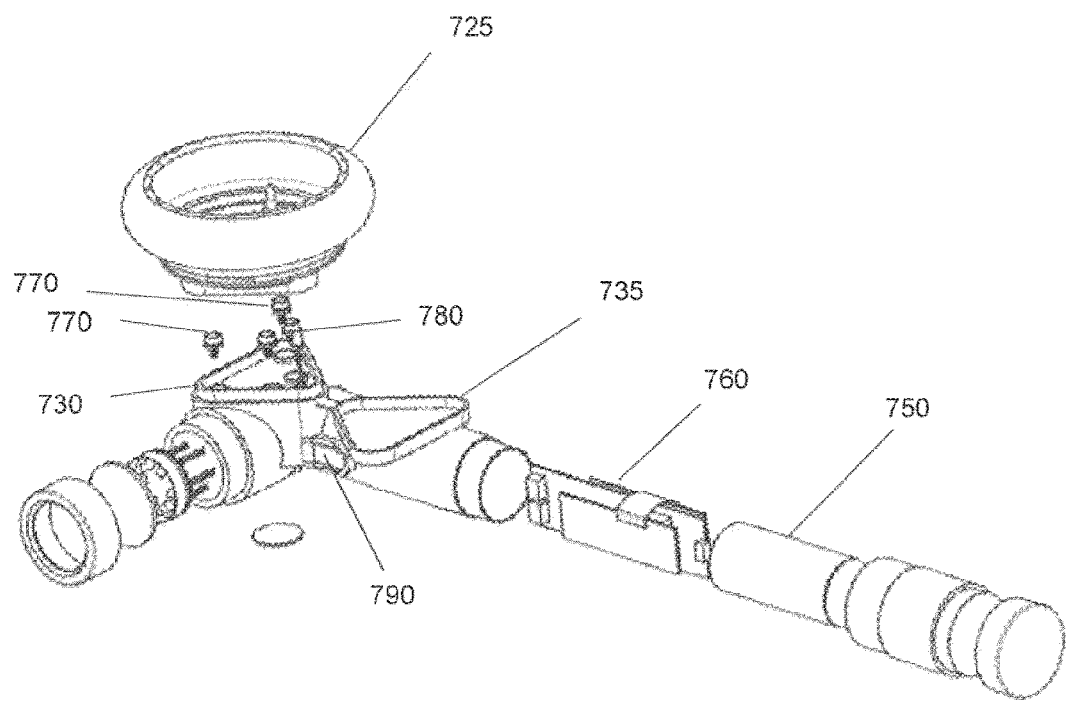
FIG. 18 is an exploded view of an optical imaging device in accordance with an embodiment of the present invention.

FIGS. 16 to 18 depict an alternative embodiment of a handheld optical imaging device 700 in accordance with the present invention. This embodiment is based on a modification of a standard issue military flashlight. In this embodiment, the optical imaging device 700 comprises a removable cap 725 attached to the main body 720 of a military flashlight, wherein the head 710 of the flashlight is provided with a cap port 730 for receiving the removable cap 725, in addition to the standard flashlight function. When not in use as an optical imaging device, the removable cap 725 is removed and the cap port 730 is covered by a port cover 735, as depicted in FIG. 17. Prior to use as an imaging device, the removable cap 725 is installed via attachment to the cap port 730.

FIG. 16 depicts the military embodiment with the removable cap 725 installed in the cap port 730.

In the embodiment depicted in FIG. 18, the device comprises one NIR light source 780, and four NIR light detectors 770.

An exploded view of this embodiment of the optical imaging device is provided in FIG. 18. FIG. 18 depicts the elongated housing that forms the main body 720 of the device 700. The housing is designed to contain within it the electronics 760 required for function, as well as the processor required to analyze the data obtained during the imaging process. A flashlight power switch 790 is provided to activate the flashlight function, and an imaging device power switch (not shown) is provided to active the imaging function. The device is powered by battery 750.

It is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

We claim:

1. A near infrared (NIR) light optical imaging device for imaging an object, the imaging device comprising:
   a body,
   at least three optical transceivers located within the body, and
   a device cap, the device cap comprising:
      a bellow support plate comprising a support plate face configured to face a surface of the object to be imaged;
      a deformable bellow sealingly engaged to the bellow support plate, and
      at least three deformable housings, each of the deformable housings being adapted to receive a light pipe and having a tip adapted to contact the surface of the object to be imaged, each of the light pipes corresponding to one of the at least three optical transceivers,
   wherein the deformable bellow has a cross-sectional profile defining a first perimeter rim and a second perimeter rim, wherein the first perimeter rim sealingly engages the bellow support plate.

2. The device according to claim 1, wherein the cross-sectional profile is a C-shaped cross-sectional profile.

3. The device according to claim 1, wherein the at least three optical transceivers is three primary optical transceivers arranged in a triangular configuration, and the at least three deformable housing is three primary deformable housings arranged in a corresponding triangular configuration.

4. The device according to claim 3, wherein the triangular configuration is an equilateral triangle.

5. The device according to claim 4, wherein the three primary optical transceivers comprise one NIR light source and two NIR light detectors.

6. The device according to claim 1, wherein the at least three optical transceivers is three primary optical transceivers arranged in an equilateral triangular configuration and two secondary optical transceivers located at the edges of equilateral triangle formed by the primary optical transceivers, and the at least three deformable housing is three primary deformable housings arranged in a corresponding equilateral triangular configuration and two secondary deformable housings located at the edges of equilateral triangle formed by the primary deformable housings.

7. The device according to claim 6, wherein the three primary optical transceivers are one NIR light source and two NIR light detectors and the two secondary optical transceivers are NIR light detectors.

8. The device according to claim 1, further comprising air inflow system for allowing passage of air from the exterior of the device into the interior of the deformable bellow when in use.

9. The device according to claim 8, wherein the air inflow system comprises one or more air flow holes between first and second support plate faces.

10. The device according to claim 9, wherein the air inflow system further comprises one or more grooves in the first perimeter rim of the deformable bellow.

11. The device according to claim 10, wherein the air inflow system further comprises one or more openings on the bellow support plate corresponding to the one or more grooves in the first perimeter rim of the deformable bellow.

12. The device according to claim 1, wherein the deformable bellow further comprises nonlinear, radially disposed grooves at the second perimeter rim.

13. The device according to claim 12, wherein the radially disposed grooves are s-shaped.

14. The device according to claim 1, wherein the bellow support plate is formed from a polymeric material.

15. The device according to claim 14, wherein the polymeric material is ABS plastic, optionally doped with a near-infrared absorbant.

16. The device according to claim 1, wherein the deformable bellow is formed from silicone polymer.

* * * * *